US008318460B2

(12) United States Patent
Cantor et al.

(10) Patent No.: US 8,318,460 B2
(45) Date of Patent: *Nov. 27, 2012

(54) HAPLOTYPE ANALYSIS

(75) Inventors: Charles R Cantor, Del Mar, CA (US); Chunming Ding, Singapore (SG)

(73) Assignee: Trustees of Boston University, Boston, MA (US)

( * ) Notice: Subject to any disclaimer, the term of this patent is extended or adjusted under 35 U.S.C. 154(b) by 131 days.

This patent is subject to a terminal disclaimer.

(21) Appl. No.: 12/704,043

(22) Filed: Feb. 11, 2010

(65) Prior Publication Data

US 2010/0184075 A1    Jul. 22, 2010

Related U.S. Application Data

(63) Continuation of application No. 10/542,043, filed as application No. PCT/US2004/001329 on Jan. 16, 2004, now Pat. No. 7,700,325.

(60) Provisional application No. 60/441,046, filed on Jan. 17, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/91.2; 435/6.1; 536/23.1; 536/24.3

(58) Field of Classification Search .................. None
See application file for complete search history.

(56) References Cited

U.S. PATENT DOCUMENTS

| 7,700,325 B2* | 4/2010 | Cantor et al. ............... 435/91.2 |
| 2002/0025532 A1 | 2/2002 | Huang |
| 2004/0081993 A1 | 4/2004 | Cantor |
| 2004/0224331 A1 | 11/2004 | Cantor |

FOREIGN PATENT DOCUMENTS

| EP | 1178119 A2 | 6/2002 |
| WO | 00/50869 A2 | 8/2000 |
| WO | 01/42496 A2 | 6/2001 |
| WO | 01/68913 | 9/2001 |
| WO | 01/75163 A2 | 10/2001 |
| WO | 01/90399 A2 | 11/2001 |
| WO | 01/96607 A2 | 12/2001 |
| WO | 02/08462 A1 | 1/2002 |

OTHER PUBLICATIONS

Buckholz et al 'Methylation Analysis at Three Different Loci Within the Imprinted Region of Chromosome 15q11-13' American Journal of Medicine Genetics 72:117-119 (1997).
Gerhard et al 'Identification of a recent recombination event within the human B-globin gene cluster' Proc. Nad. Acad. Sci. USA vol. 81, pp. 7875-7879, Dec. 1984.
Furlong, RA 'Analysis of four microsattelite markers on the long arm of chromosome 9 by meiotic recombination in flow-sorted single sperm.' Am J Hum Genet. Jun. 1993;52(6):1191-1199.
Braun et al., "Improved Analysis of Microsatellites Using Mass Spectrometry." Genomics 46:18-23, 1997.
Buchanan, FC et al., "Association of a missense mutation in the bovine leptin gene with carcass fat content and leptin MRNA levels." Genetics Selection Evolution, EDP Sciences, Les Ulis., FR 34(1):105-116, 2002.
Sauer et al., "Facile method for automated genotyping of single nucleotide polymorphisms by mass spectrometry." Nucleic Acids Research 30(5):1-5, e22, 2002.
Suomalainen, A and AC Syvänen, "Quantitative analysis of human DNA sequences by PCR and solid-phase minisequencing." Mol Biotechnol 15(2):123-131, 2000.
Tang, et al., "Single nucleotide polymorphism analyses by MALDI-TOF MS." International Journal of Mass Spectrometry 226:37-54, 2003.
Amexis, et al., "Quantitative mutant analysis of viral quasispecies by chip-based matrix-assisted laser desorption/ionization time-of-flight ight mass spectrometry," PNAS 98(21):12097-12102, 2001.
Amexis, et al., "Sequence diversity of Jeryl Lynn strain of mumps virus: quantitative mutant analysis for vaccine quality control." Virology 300(2):171-179, 2002.
Becker-André, M. and Hahlbrock, K., "Absolute mRNA quantification using the polymerase chain reaction (PCR). A novel approach by a PCR aided transcript titration assay (PATTY)." Nucleic Acids Research 17(22):9437-9446, 1989.
Böcker, "SNP and mutation discover using base-specific cleavage and MALDI-TOF mass spectrometry." Bioinformatics 19(Suppl 1):i44-i53, 2003.
Cheng et al., "Effective amplification of long targets from cloned inserts and human genomic DNA." PNAS 91:5695-5699, 1994.
Doris et al., "Quantitative analysis of gene expression by ion-pair high-performance liquid chromatography." J Chromatography A 806(1):47-60, 1998.
Elso et al., "Mutation Detection Using Mass Spectrometric Separation of Tiny Oligonucleotide Fragments." Genome Research 12:1428-1433, 2002.
Landegren et al. "Reading Bits of Genetic Information: Methods for Single-Nucleotide Polymorphism Analysis." Genome Research 8:769-776, 1998.
Nakai et al., "Highly multiplexed genotyping of coronary artery disease-associated SNPs using MALDI-TOF mass spectrometry." Human Mutation 20:133-138, 2002.

(Continued)

*Primary Examiner* — Stephen Kapushoc
(74) *Attorney, Agent, or Firm* — Nixon Peabody LLP; Ronald I. Eisenstein; Leena H. Karttunen Contarino

(57) ABSTRACT

The present invention provides an efficient way for high throughput haplotype analysis. Several polymorphic nucleic acid markers, such as SNPs, can be simultaneously and reliably determined through multiplex PCR of single nucleic acid molecules in several parallel single molecule dilutions and the consequent statistical analysis of the results from these parallel single molecule multiplex PCR reactions results in reliable determination of haplotypes present in the subject. The nucleic acid markers can be of any distance to each other on the chromosome. In addition, an approach wherein overlapping DNA markers are analyzed can be used to link smaller haplotypes into larger haplotypes. Consequently, the invention provides a powerful new tool for diagnostic haplotyping and identifying novel haplotypes.

26 Claims, 3 Drawing Sheets

OTHER PUBLICATIONS

Ross et al., "Quantitative Approach to Single-Nucleotide Polymorphism Analysis Using MALDI-TOF Mass Spectrometry," BioTechniques 29(3):620-629, 2000.
Barnes, W.M., Proc. Natl. Acad. Sci. USA 91:2216-2220 (1994).
Clark, A.G., Mol. Biol. Evol. 7(2):111-122 (1990).
Collins et al., Science 278(5343):1580-1581 (1997).
Conner et al., Proc. Natl. Acad. Sci. USA 80:278-282 (1983).
Daly et al., Nature Genetics 29:229-232 (2001).
Ding et al., PNAS 100(13):7449-7453 (2003).
Douglas et al., Nature Genetics 28:361-364 (2001).
Drysdale et al., Proc. Natl. Acad. Sci. USA 97(19):10483-10488 (2000).
Evans et al, Science 286:487-491 (1999).
Gabriel et al., Science 296:2225-2229 (2002).
Grupe et al., Science 292:1915-1918 (2001).
Hirschhorn et al., Genetics in Medicine 4(2):45-61 (2002).
Hodge et al., Nature Genetics 21:360-361 (1999).
Jeffreys et al., Cell 60:473-485 (1990).
Jeffreys et al., Nucleic Acids Res. 16(23):10953-10971 (1988).
Judson et al., Pharmacogenomics 1(1):15-26 (2000).
Kruglyak, L., Nature Genetics 22:139-144 (1999).
Krynetski & Evans, Am. J. Hum. Genet. 63:11-16 (1998).
Martin et al., Genomics 63:7-12 (2000).
Michalatos-Beloin et al., Nucleic Acids Res. 24(23):4841-4843 (1996).
Nickerson et al., Proc. Natl. Acad. Sci. USA 87:8923-8927 (1990).
Orita et al., Proc. Natl. Acad. Sci. USA 86:2766-2770 (1989).
Papadopoulos et al., Nature Genetics 11:99-102 (1995).
Prior et al., Human Mutation 5:263-268 (1995).
Rein et al., Nucleic Acids Res. 26(10):2255-2264 (1998).
Ross et al., Nature Biotechnology 16:1347-1351 (1998).
Ruano et al., Nucleic Acids Res. 17(20):8392 (1989).
Ruano et al., Nucleic Acids Res. 19(24):6877-6882 (1991).
Ruano et al., Proc. Natl. Acad. Sci. USA 87:6296-6300 (1990).
Shields & Harris, J. Clin.l Oncol. 18(11):2309-2315 (2000).
Stephens et al., Am. J. Hum. Genet. 46:1149-1155 (1990).
Stephens et al., Am. J. Hum. Genet. 68:978-989 (2001).
Templeton et al., Genetics 120:1145-1154 (1988).
Woolley et al., Nature Biotechnology 18:760-763 (2000).
Zhang et al., Am. J. Hum. Genet. 69:904-914 (2001).

* cited by examiner

SEQUENCE LISTING

<160> NUMBER OF SEQ ID NOS: 48

<210> SEQ ID NO 1

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tctaccagct tggctccctc                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagtccatca gcagcagcag                                                  20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggagtcagc ccagctc                                                     17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actggtgaga caatcccttc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccactggcat taaagtgctg                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agccacagaa gaaggactcc                                                  20

<210> SEQ ID NO 7
<211> LENGTH: 20
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 7
taccagaaac cagacctctg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtgctggac agaaagtgag                                                 20

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgaggatggt gggaggg                                                    17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tctaccagaa accagacctc                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agtgctggac agaaagtgag                                                 20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acctctgagg gccccttac                                                  19

<210> SEQ ID NO 13
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
ctcgagtgat aatctcaggg                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggtagtgtt tacagccctc                                                  20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgatgatgtc gaagaggctc atg                                              23

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttacgagaca tgacctcagg                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcatttgatt ggcagagcag                                                  20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgcaggaag ctctggatg                                                   19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 19
gcatttgatt ggcagagcag                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttacgagaca tgacctcagg                                                    20

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agagcagctc cgagtcc                                                       17

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcagcacata ctggaaatcc                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttctctccc caggatatcg                                                    20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24 gcttttctt agaataggag g                                                   21

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
```
agatcttggg catcttgagg                                      20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acccctgtct tccacaggtt                                      20

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgggcctggc tggggaagc                                       19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acccctgtct tccacaggtt                                      20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
agatcttggg catcttgagg                                      20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgtcttccac aggttgtcgg c                                    21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gtaaaactgc agctgaggag                                      20

```
<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgactaggtc aggtcccctc                                              20

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggagtattta aaggagagac acactag                                      27

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgactaggtc aggtcccctc                                              20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtaaaactgc agctgaggag                                              20

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccctcgtgcc acagcct                                                 17

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggacatcaaa ggaacaggac                                              20
```

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
actcacaata ttgggcaggc                                              20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caaggggcta agggagaag                                               19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggttgcatg agcattaagt                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cacatcaagg ataagactgc                                              20

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atctcttcag tagacgaac                                               19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tggccttgat tcaaaccctg                                              20

<210> SEQ ID NO 44
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
agatgaagga aatcccaagg                                                  20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgccactaac atacatagta ac                                               22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccttggcttg atagtcaaac                                                  20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atttggagga gtgcagagag                                                  20

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agtcaaactc tcaccac                                                     17
```

HAPLOTYPE ANALYSIS

CROSS-REFERENCE TO RELATED APPLICATIONS

The present application is a Continuation of U.S. Utility Application Ser. No. 10/542,043, which issued as U.S. Pat. No. 7,700,325, which is a 371 National Stage of International Application No. PCT/US04/01329 filed on Jan. 16, 2004, which designated the U.S., and which claims benefit under 35 U.S.C. §119(e) of the U.S. provisional application Ser. No. 60/441,046, filed Jan. 17, 2003.

BACKGROUND OF THE INVENTION

Genetic polymorphisms are well recognized mechanisms underlying inter-individual differences in disease risk as well as treatment response in humans (Evans and Relling (1999) Science 286:487-491; Shields and Harris (2000) J. Clin. Onc. 18:2309-2316). Single nucleotide polymorphism (SNP) analysis has drawn much attention with the hope of identifying genetic markers for and genes involved in common diseases because of the frequency of the SNPs. Also, for many genes, the detection of SNPs known to confer loss of function provides a simple molecular diagnostic to select optimal medications and dosages for individual patients (Evans and Relling (1999) Science 286:487-491). It is common for genes to contain multiple SNPs, with haplotype structure being the principal determinant of phenotypic consequences (Collins et al. (1997) Science 278, 1580-81; Drysdale et al. (2000) Proc. Natl. Acad. Sci. 97:10483-8; Krynetski and Evans (1998) Am. J. Hum. Gen. 63:11-16). Therefore, to more accurately associate disease risks and pharmacogenomic traits with genetic polymorphisms, reliable methods are needed to unambiguously determine haplotype structure for multiple SNPs or other nucleic acid polymorphisms or mutations within genes as well as non-coding genomic regions.

However, current genotyping technologies are only able to determine each polymorphism, including SNPs, separately. In other words, there is a lack of information on how several polymorphisms are associated with each other physically on a chromosome. A DNA haplotype, the phase determined association of several polymorphic markers (e.g., SNPs) is a statistically much more powerful method for disease association studies. Yet unfortunately, it is also much harder to determine a haplotype. Current experimental approaches include a physical separation of homologous chromosomes via means of mouse cell line hybrid, cloning into a plasmid and allele specific PCR. Neither of them is simple enough a method for routine high-throughput analysis. There are also ways to computationally determine haplotypes, but the accuracy of such computational analysis is uncertain.

Approaches that can be used to haplotype SNPs or other nucleic acid polymorphisms, modifications and/or mutations that reside within relatively close proximity include, but are not limited to, single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). A major drawback to these procedures is that they are limited to polymorphism detection along short segments of DNA and typically require stringent reaction conditions and/or labeling. Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive, but these methods are also limited to haplotyping SNPs along short DNA segments (<1 kb) (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

Long-range PCR (LR-PCR) offers the potential to haplotype SNPs that are separated by kilobase lengths of genomic DNA. LR-PCR products are commonly genotyped for SNPs, and haplotypes inferred using mathematical approaches (e.g., Clark's algorithm (Clark (1990) Mol. Biol. Evol. 7:111-122). However, inferring haplotypes in this manner does not yield unambiguous haplotype assignment when individuals are heterozygous at two or more loci (Hodge et al. (1999) Nature Genet. 21:360-361). Physically separating alleles by cloning, followed by sequencing, eliminates any ambiguity, but this method is laborious and expensive. Long-range allele-specific amplification negates both of these problems, but is limited to SNP-containing alleles that have heterozygous insertion/deletion anchors for PCR primers (Michalatos-Beloin et al. (1996) Nucleic Acids Res. 24:4841-4843). More complex technologies have also been used, such as monoallelic mutation analysis (MAMA) (Papadopoulos et al. (1995) Nature Genet. 11:99-102) and carbon nanotube probes (Woolley et al. (2000) Nature Biotech. 18:760-763), but these are either time consuming (MAMA), or require technology that is not widely available (nanotubes). U.S. Patent Application No. US 2002/0081598 discloses a haplotyping method which involves the use of PCR amplification and DNA ligation to bring the polymorphic nucleic acid sites in a particular allele into close proximity to facilitate the determination of haplotypes spanning kilobase distances. However, this method relies on at least two enzymatic steps to create DNA fragments that can be ligated with other DNA fragments, and subsequently ligases to combine the DNA fragments to form one large fragment with several polymorphic sites in a shorter distance. These additional sample preparation steps make large scale use and automation of this technique cumbersome and error prone.

Haplotypes, combinations of several phase-determined polymorphic markers in a chromosome, are extremely valuable for studies like disease association[1,2] and chromosome evolution. Direct molecular haplotyping has relied heavily on family data, but is limited to short genomic regions (a few kilobases). Statistical estimation of haplotype frequencies can be inconclusive and inaccurate[3].

With the rapid discovery and validation of several million single nucleotide polymorphisms (SNP), it is now increasingly practical to use genome-wide scanning to find genes associated with common diseases[1,2]. However, individual SNPs have limited statistical power for locating disease susceptibility genes. Haplotypes can provide additional statistical power in the mapping of disease genes[4-7].

Haplotype determination of several markers for a diploid cell is complicated since conventional genotyping techniques cannot determine the phases of several different markers. For example, a genomic region with three heterozygous markers can yield 8 possible haplotypes. This ambiguity can, in some cases, be solved if pedigree genotypes are available. However, even for a haplotype of only 3 markers, genotypes of father-mother-offspring trios can fail to yield offspring haplotypes up to 24% of the time. Computational algorithms such as expectation-maximization (EM), subtraction and PHASE are used for statistical estimation of haplotypes[4,8,9]. However, these computational methods have serious limitations in accuracy, number of markers and genomic DNA length. For example, for a haplotype of only 3 markers from doubly heterozygous individuals, the error rates of the EM and PHASE methods for haplotype reconstruction can be as high as 27% and 19%, respectively[3]. Alternatively, direct molecular haplotyping can be used based on the physical separation of two homologous genomic DNAs prior to genotyping. DNA cloning, somatic cell hybrid construction, allele specific PCR and single molecule PCR[10-12] have been used, and these approaches are largely independent of pedigree information. These methods are limited to short genomic regions (allele-specific PCR and single molecule PCR) and are prone to errors.

Therefore, a simple and more reliable method, which is also suitable for large scale and automated haplotype determination of several polymorphic alleles separated by several kilobase distances is needed to facilitate the analysis of haplotype structure in pharmacogenomic, disease pathogenesis, and molecular epidemiological studies.

SUMMARY OF THE INVENTION

The present invention provides an efficient way for high throughput haplotype analysis. Several polymorphic nucleic acid markers, such as SNPs, can be simultaneously and reliably determined through multiplex PCR of single nucleic acid molecules in several parallel single molecule dilutions and the consequent statistical analysis of the results from these parallel single molecule multiplex PCR reactions results in reliable determination of haplotypes present in the subject. The nucleic acid markers can be of any distance to each other on the chromosome. In addition, an approach wherein overlapping DNA markers are analyzed can be used to link smaller haplotypes into larger haplotypes. Consequently, the invention provides a powerful new tool for diagnostic haplotyping and identifying novel haplotypes.

The method of the present invention enables direct molecular haplotyping of several polymorphic markers separated by several kilobases even spanning an entire chromosome. Distances of about 1, 2, 3, 4, 5-10, 15-20, kilobases (kb) or as far as about at least 25, 30, 35, 40, 45, or 50 kb or more are preferred.

Polymorphic nucleic acids useful according to the present invention include any polymorphic nucleic acids in any given nucleic acid region including, but not limited to, single nucleotide substitutions (single nucleotide polymorphisms or SNPs), multiple nucleotide substitutions, deletions, insertions, inversions, short tandem repeats including, for example, di-, tri-, and tetra-nucleotide repeats, and methylation and other polymorphic nucleic acid modification differences. Preferably the polymorphic nucleotides are SNPs.

A nucleic acid sample, preferably genomic nucleic acid sample from a subject organism is first diluted to a single copy dilution. The phrase "single copy dilution" refers to a dilution wherein substantially only one molecule of nucleic acid is present or wherein one or more copies of the same allele are present. When the molecular mass of the nucleic acid is known, a dilution resulting in one single molecule dilution can be readily calculated by a skilled artisan. For example, for human genomic DNA, about 3 pg of DNA represents about one molecule. Due to stochastic fluctuation in very dilute DNA solutions, the diluted sample may have no template nucleic acid molecules or it may have two or more molecules. If no molecules are present in the sample, PCR amplification will not be achieved and the result will be "no genotype". If two or more molecules are present in the sample, the resulting amplification products may either be a mixture of two different alleles or represent one allele and consequently either a mixed genotype or a single allele genotype, respectively, is obtained.

To obtain statistical weight to accurately determine the haplotype comprising at least two markers, more than one replica of dilutions will be needed. For example, a replicate of four independent multiplex genotyping assays using about 3-4.5 pg of human genomic DNA, including the steps of diluting the nucleic acid sample, amplifying the diluted sample, and genotyping the amplified sample, enables about 90% of direct haplotyping efficiency. Therefore, preferably at least about 4-25, more preferably at least about 6-20, 8-20, 10-18, 12-18 and most preferably about 10-12 replicates of same sample are included in the analysis according to the present invention, one replica including the steps of diluting the isolated nucleic acid sample from a subject organism, multiplex amplification of the diluted sample and genotyping the polymorphic nucleic acid sites from the amplified sample.

After the step of diluting the nucleic acid sample into a substantially single nucleic acid dilution, the regions containing the polymorphic sites of interest in the nucleic acid are amplified, using, for example polymerase chain reaction (PCR) and at least two, preferably more than two primer pairs flanking at least two different polymorphic nucleic acid sites in the target molecule. The primers are selected so that they amplify a fragment of at least about 50 base pairs (bp), more preferably at least about 100, 200, 300, 400, 500, 600-1000 bp and up to about 10000 bp, wherein the fragment contains at least one polymorphic nucleotide site. Most preferably, the primer pairs are designed so that the amplification products are about 90-350 bp long, still more preferably about 100-250 bp long. It is preferable to maximize the efficiency of amplification from the single molecule template and therefore, at least with the current technology, the shorter fragments are preferred. However, it will be self evident to a skilled artisan that the nucleic acid amplification techniques are constantly developing and the efficiency of amplifying longer nucleic acid fragments using very small quantities of template can be perfected and consequently, primers amplifying long fragments, even longer that those indicated above, may also be used according to the present invention.

After the amplification of the single molecule template with at least two different primer pairs, preferably at least 3, 4, 5, 6, 7, 8, 9, 10, primer pairs are used in a multiplex amplification reaction, the amplification product is subjected to genotyping. Use of up to at least about 15, 20, 30, 40, 50 or more primer pairs in one multiplex reaction is preferred on one embodiment of the invention.

Genotyping can be performed by any means known to one skilled in the art including, for example, restriction fragment length polymorphism (RFLP) analysis using restriction enzymes, single-strand conformational polymorphism (SSCP) analysis, heteroduplex analysis, chemical cleavage analysis, oligonucleotide ligation and hybridization assays, allele-specific amplification, solid-phase minisequencing, or MASSARRAY™ system.

The haplotype is subsequently determined by analyzing replicas of at least four dilution/amplification/genotyping reactions so as to allow statistically accurate determination of the correct haplotype in the subject. The steps including dilution, amplification and genotyping from the same subject organism sample are repeated several times to obtain a data set which can be statistically analyzed to reveal the correct haplotype in the subject organism's sample. The approach does not rely on pedigree data and does not require prior amplification of the genomic region containing the selected markers thereby simplifying the analysis and allowing speedy and automated haplotyping.

In one embodiment, the invention is drawn to methods for determining a novel haplotype of nucleic acid segments, particularly of genes or other contiguous nucleic acid segments comprising at least two, preferably at least 3, 4, 5, 6, 7, 8, 9, 10-15, 20, 30, 40, 50-100 or even more distantly spaced nucleic acid polymorphisms.

The methods of the present invention are useful in medicine in determining the differences in disease risk or susceptibility and determining treatment response between individual patients. The methods, however, are not limited to applications in medicine and can be used to determine the haplotype structure of a particular gene, or other contiguous DNA segment, within an organism having at least two distally spaced nucleotide polymorphisms. Thus, the methods of the invention find further use in the field of agriculture, particularly in the breeding of improved livestock and crop plants.

In one embodiment, the invention provides a method of determining a haplotype in a sample obtained from an organism and comparing it to known haplotypes to diagnose a disease or disease susceptibility of an organism comprising the steps of identifying at least two polymorphic markers within a genomic region; isolating a nucleic acid sample from the subject organism and preferably purifying the isolated nucleic acid; diluting the nucleic acid sample into substantially single molecule dilution; amplifying the diluted nucleic acid sample with at least two primer pairs each capable of amplifying a different region flanking each of the polymorphic sites in a multiplex PCR reaction; genotyping the polymorphic sites from the amplified sample; producing at least three additional genotype replicas from the nucleic acid sample of the subject organism as described above to allow statistically accurate determination of the haplotype in the subject organism sample. In a preferred method the genotyping is performed using primer extension, terminator nucleotides and matrix-assisted laser desorption/ionization time-of-flight mass spectrometry MALDI-TOF MS analysis. The haplotype is thereafter compared to an existing haplotype collection such as a haplotype database comprising disease- or disease susceptibility-associated haplotypes, or haplotypes associated with treatment responsiveness or unresponsiveness of the specific polymorphic markers. An non-limiting example of an existing haplotype database is a Y-STR Haplotype Reference Database which can be found at world wide web address ystr dot charite dot de.

For example, the R117H mutation in the cystic fibrosis transmembrane receptor (CFTR) gene shows mild effect without the 5T mutation, and severe effect when the 5T mutation is present on the same chromosome. Thus, a haplotype of R117H-5T is important for clinical application to determine the severity of the prognosis of this type of cystic fibrosis. The method of the present invention allows direct determination of the haplotypes with no requirement for patient pedigree genotype information, i.e. information of the genotypes from the patient's family members. The same approach can be applied in other genetic diseases where, for example, a second mutation on the same chromosome can change the disease manifestation from the first mutation.

The invention further provides a method wherein two haplotypes comprising several different polymorphic markers can be combined to form a larger haplotype covering a larger genomic region. This can be achieved by using one or more primer pairs to amplify one common polymorphic marker in two parallel multiplex amplification reactions after first diluting the sample as described above. The genotyping is performed as described above and the overlapping marker(s) provide a means to combine the two smaller haplotypes into one larger large haplotype comprising all the markers analyzed in both of the two different multiplex amplification reactions.

In one embodiment, the present invention provides a method for constructing a database of haplotypes associated with one or more disease or biological trait using the methods described above. Such haplotype databases are useful for diagnostic and prognostic applications. A haplotype obtained from a subject organism suspected can be compared against the haplotype database and allows diagnosis and/or prognosis of a condition of interest. A condition may be a disease condition or a biochemical or other biological trait which is associated, for example, in responsiveness to a particular treatment or pharmaceutical and is determinative of choosing a treatment regime that, for example, a human patient would be responsive to.

In one embodiment, the polymorphism is a nucleic acid modification, such as a methylation difference. For example, in one embodiment, the present invention provides a method of determining haplotypes comprised of markers including methylation differences. The DNA sample can be treated with any composition, for example, inorganic or organic compounds, enzymes, etc., that differentially affects the modified, for example, methylated, nucleotide to effectively create polymorphisms based on methylation states. For example, DNA sample is treated with bisulfite (Frommer, M., L. E. McDonald, D. S. Millar, C. M. Collis, F. Watt, G. W. Grigg, P. L. Molloy, and C. L. Paul. 1992. A genomic sequencing protocol that yields a positive display of 5-methylcytosine residues in individual DNA strands. Proc. Natl. Acad. Sci U.S.A. 89:1827-1831) so that unmethylated cytosine residues are converted into uracil while methylated cytosines remain the same, thus effectively creating polymorphisms based on methylation states. Haplotypes consisting polymorphisms in the DNA region next to the methylation region and the methylation region itself can be determined in a similar fashion as described above. Bisulfite treated DNA is diluted to approximately single copy, amplified by multiplex PCR (each PCR specific for each polymorphism), and genotyped by the MassARRAY system.

The methylation detection procedure as described above is repeated at least 3, 4, 5, 6, 7, 8, 9, 10-15, 15-20, 30, 40, 50 or more times, preferably about 12-18 times so as to allow statistical analysis of the correct methylation haplotype in the subject organism.

In the preferred embodiment, the methods of the present invention use mass spectrometry, for example, MASSARRAY™ system, to genotype the samples.

Therefore in one embodiment, the present invention provides a method for determining a haplotype of a subject comprising the steps of diluting a nucleic acid sample from the subject into a single molecule dilution; amplifying the diluted single nucleotide dilution with at least two different primer pairs designed to amplify a region comprising at least two polymorphic sites in the nucleic acid template; genotyping the polymorphic sites in the single nucleic acid molecule; and determining the haplotype from the genotypes of at least the two polymorphic sites to obtain a haplotype for the subject.

In one embodiment, the steps of diluting, amplifying and genotyping the nucleic acid sample from the subject are repeated at least three times from the same nucleic acid sample to obtain at least four genotype replicas from the same subject and thereafter comparing the at least four genotype replicas to determine the haplotype. Preferably, at least 4, 5, 6, 7, 8-10, 10-15, 15-20, 30, 50, 50-100 or more genotype replicas are obtained. In one embodiment about 12-18 replicas are obtained and the results are analyzed statistically, using for example a method of Poisson distribution.

In one embodiment, the method further comprises comparing the haplotype with a haplotype from a control or a database of haplotypes from controls to determine association of the haplotype with a biological trait, which can be any biological trait including but not limited to various diseases.

The polymorphisms useful according to the present invention include, but are not limited to single nucleotide polymorphisms (SNPs), deletions, insertions, substitutions or inversions. The polymorphisms may also be a combination of one or more markers selected from the group consisting of a single nucleotide polymorphism, deletion, an insertion, a substitution or an inversion or other types of nucleic acid polymorphisms.

In one embodiment, the genotyping step of the method described above is performed using primer extension, preferably MASSARRAY™ technology, and mass spectrometric detection, preferably MALDI-TOF mass spectrometry.

In another embodiment, the invention provides a method of diagnosing a disease condition or disease susceptibility by determining a disease related haplotype in a subject comprising the steps of diluting a nucleic acid sample from the subject into a single molecule dilution; amplifying the diluted single nucleotide dilution with at least two primer pairs designed to amplify a region comprising at least two polymorphic sites in the nucleic acid template; genotyping the polymorphic sites in the single nucleic acid molecule; determining the haplotype from the genotype of at least two polymorphic sites to obtain a haplotype for the subject; and comparing the haplotype of the subject to known disease-associated haplotypes wherein a match in the sample haplotype with a disease-associated haplotype indicates that the subject has the disease or that the subject is susceptible for the disease.

In one embodiment, the method further comprises repeating the dilution, amplification and genotyping steps at least three times from the same nucleic acid sample to obtain at least four genotype replicas from the same subject and thereafter comparing the at least four genotype replicas to determine the haplotype. Preferably at least 4, 5, 6, 7, 8, 9, 10-15, 15-20, 25, 30, 40, 50-100 or more genotype replicas are produced. In one embodiment, about 12-18 replicas are produced.

The invention also provides a method of determining a haplotype of a subject comprising the steps of treating a nucleic acid sample from the subject with a composition that differentially affects an epigenetically modified nucleotide in the nucleic acid sample to effectively create polymorphisms based on the epigenetic modification; diluting the treated nucleic acid sample into a single copy dilution; amplifying the diluted nucleic acid sample using at least two different primer pairs; genotyping the amplified sample; and determining the haplotype of the subject from the genotyped sample. The terms "epigenetic" modification or "epigenetically" modified nucleotides as described herein means nucleic acids that are modified by methylation, acetylation, or other epigenetic manner, i.e. by addition or deletion of a chemical or molecular structure on the nucleic acid which addition or deletion has an effect on the phenotype of the subject by altering the function of the modified nucleic acid.

In one embodiment, the method further comprises repeating the steps of dilution, amplification and genotyping at least three times to obtain at least four genotype replicas from the same subject and thereafter determining a haplotype of the subject based on the genotype replicas. In a preferred embodiment, at least 4, 5, 6, 7, 8, 9, 10-15, 15-20, 25, 30, 40, 50-100, or more replicas are produced. In one preferred embodiment, about 12-18 replicas are produced. The method of claim 13, wherein 12-18 replicas are produced.

In one embodiment, the epigenetic modification is methylation.

In yet another embodiment, the epigenetic modification is methylation and the composition that is used to treat the nucleic acid is bisulfite.

In another embodiment, the invention provides a method of determining a haplotype in a subject comprising the steps of: digesting a nucleic acid sample from the subject with a methylation-sensitive restriction enzyme so that either unmethylated DNA or methylated DNA is left intact, depending on which enzyme is used; diluting the digested nucleic acid sample to a single molecule concentration; amplifying the diluted nucleic acid sample with at least two different primer pairs; genotyping the amplified sample; and determining a haplotype of a methylated nucleic acid wherein at least two polymorphic markers next to the methylation site, together with the methylation site, constitutes a haplotype.

In one embodiment, the methylation sensitive enzyme is HpaII.

In one embodiment, the method further comprises repeating the steps of diluting, amplifying and genotyping at least three times to obtain at least four genotype replicas from the same subject and thereafter determining a haplotype of the subject based on the genotype replicas. Preferably at least 4, 5, 6, 7, 8, 9, 10-15, 4, 5, 6, 7, 8, 9, 10-15,15-20, 25, 30, 40, 50-100, or more replicas are produced. In one preferred embodiment, about 12-18 replicas are produced. The method of claim 13, wherein 12-18 replicas are produced.

DETAILED DESCRIPTION OF THE INVENTION

Figure 1A:
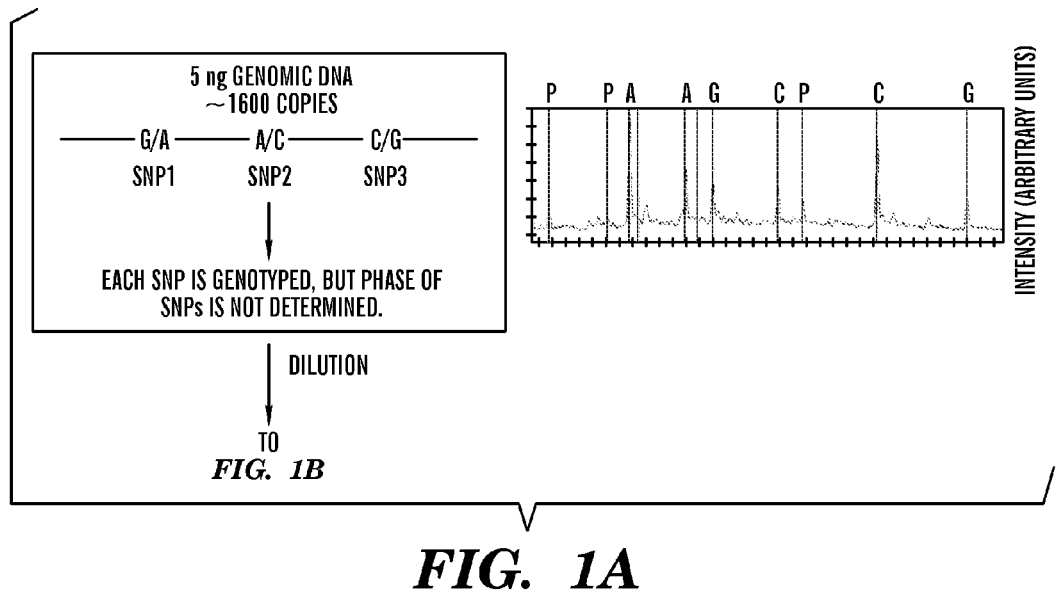
FIGS. 1A-1B show a flow chart of multiplex genotyping of single DNA molecules for haplotype analysis using single nucleotide polymorphisms (SNPs) as markers. Traditional genotyping methods using a few nano-grams (ng) genomic DNA (about 1600 copies of genomic templates) yield only the genotypes of each individual SNP marker, but the phases of these SNPs are not determined (shown in top right in the mass spectra in FIG. 1A). Simultaneous genotyping of several markers using multiplex assays with single DNA molecules (FIG. 1B) allows haplotyping analysis since the two alleles can be physically separated with very dilute DNA concentrations, shown in bottom right in the mass spectra in FIG. 1B. In contrast to other molecular haplotyping methods, the entire haplotype block does not have to be amplified in this approach. Instead, only about 100 bp around each individual SNP is amplified for genotyping, resulting in very high efficiency of PCR amplification from single DNA molecules. The SNP markers can be as far apart as desired, as long as there is no significant break between them.
Figure 1B:
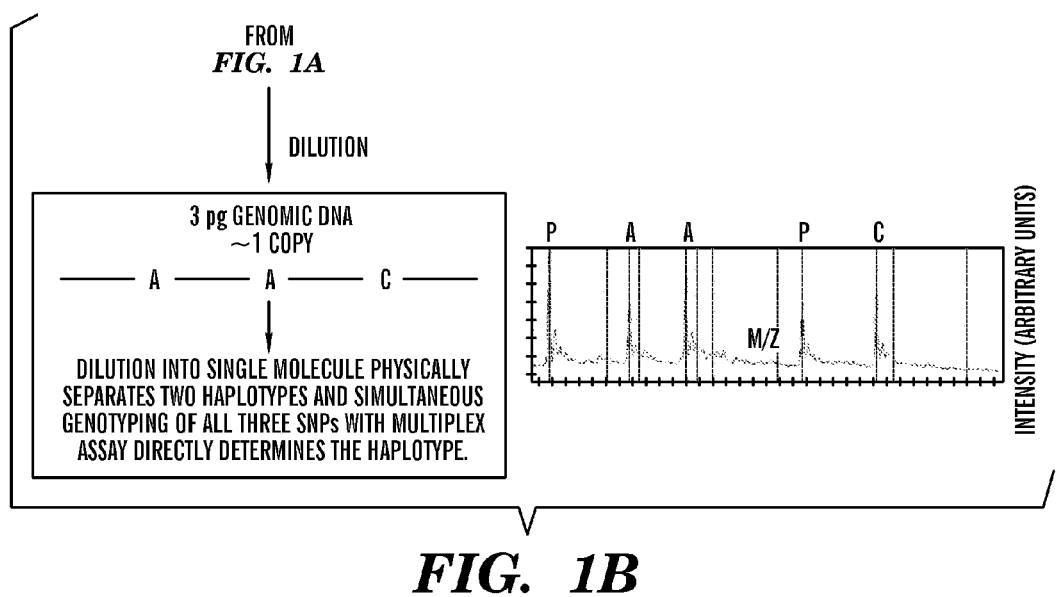

The present invention provides a direct molecule haplotyping approach which is based upon a surprising discovery that a single molecule dilution of genomic DNA can be used for separation of two homologous genomic DNAs and that using repeated dilutions from the same subject organisms as a starting material for multiplex amplification of different nucleic acid markers, haplotypes of any subject organisms can be determined and are statistically accurate. The diluted, amplified sample is then genotyped using, for example, the MASSARRAY™ system (FIG. 1). Parallel genotyping of several different dilutions from the same subject results in statistically accurate haplotype determination in the subject organism.

The approach of the present invention differs significantly from previous single molecule PCR method in that the method of the present invention does not require the amplification of the complete genomic region containing the markers of interest; thus it is not limited to only a few kb DNA. The method of the present invention achieves close to 100% genotype and haplotype success rates for single DNA molecules. Additionally, the multiplex genotyping assay approach enables direct haplotype determination without pedigree genotype information. High throughput haplotyping can easily be achieved by incorporating the method of the present invention with any commercially available genotyping systems, such as the MASSARRAY™ system.

In one embodiment, the invention provides a method of determining a haplotype of a subject comprising the steps of obtaining a nucleic acid, preferably a genomic DNA sample, diluting the nucleic acid sample into substantially a single molecule dilution, amplifying the nucleic acid sample with at least two primer pairs designed to amplify a genomic region containing a nucleic acid polymorphism on one chromosome and genotyping the amplified DNA. Repeating the steps from diluting the nucleic acid sample, at least 3 or more times and statistically analyzing the results, thereby determining the haplotype of the subject organisms.

The "subject" as used in the specification refers to any organism with at least diploid genome including, but not limited to worms, fish, insects, plants, murine and other mammals including domestic animals such as cows, horse, dogs, cats, and, most preferably humans.

The methods of the present invention are useful, for example, in diagnosing or determining a prognosis in a disease condition known to be associated with a specific haplotype(s), to map a disease or other biological trait the cause of which is currently unknown to a defined chromosomal region using haplotypes in the linkage analysis, to determine novel haplotypes, to detect haplotype associations with responsiveness to pharmaceuticals.

Genomic DNA can be obtained or isolated from a subject using any method of DNA isolation known to one skilled in the art. Examples of DNA isolation methods can be found in general laboratory manuals, such as Sambrook and Russel, MOLECULAR CLONING: A LABORATORY MANUAL, 3rd Ed., Cold Spring Harbor Laboratory Press, Cold Spring Harbor, N.Y. (2001), the entirety of which is herein incorporated by reference.

Polymorphic Markers and Oligonucleotides. The number of polymorphic nucleic acid useful according to the present invention is ever increasing. Currently, such markers are readily available from a variety of publicly accessible databases and new ones are constantly being added to the pool of available markers. Markers including restriction length polymorphisms, short tandem repeats such as di-, tri-, and tetranucleotide repeats as well as methylation status can be used as polymorphic markers according to the present invention. Such markers are well known to one skilled in the art and can be found in various publications and databases including, for example, ATCC short tandem repeat (STR) database at world wide web address atcc dot org.

Particularly useful markers according to the present invention are single nucleotide polymorphisms (SNPs). Examples of useful SNP databases include, but are not limited to Human SNP Database at world wide web address wi dot mit dot edu, NCBI dbSNP Home Page at world wide web address ncbi dot nlm dot nih dot gov, world wide web address lifesciences dot perkinelmer dot com, Celera Human SNP database at world wide web address celera dot com, the SNP Database of the Genome Analysis Group (GAN) at world wide web address gan dot iarc dot fr.

A number of nucleic acid primers are already available to amplify DNA fragments containing the polymorphisms and their sequences can be obtained, for example, from the above-identified databases. Additional primers can also be designed, for example, using a method similar to that published by Vieux, E. F., Kwok, P-Y and Miller, R. D. in BioTechniques (June 2002) Vol. 32. Supplement: "SNPs: Discovery of Marker Disease, pp. 28-32. Novel SNPs can also be identified using a method of MASSARRAY™ Discovery-RT (SNP-Discovery) system by SEQUENOM Inc. (San Diego, Calif.).

A number of different nucleotide polymorphism genotyping methods useful according to the present invention are known to one skilled in the art. Methods such as restriction length polymorphism analysis (RFLP), single-strand conformation polymorphism (SSCP) analysis, denaturing gradient gel electrophoresis (DGGE), temperature gradient gel electrophoresis (TGGE), chemical cleavage analysis, direct sequencing of nucleic acids using labels including but not limited to fluorescent and radioactive labels. All these methods have been available or at least a decade and are well known to one skilled in the art.

SNP genotyping can be performed using a number of different techniques known to one skilled in the art. For example, SNP genotyping by MALDI-TOF mass spectrometry can performed using, for example, the Sequenom's mass spectrometry system, MASSARRAY™. In this method, after multiplexed PCR has been performed using more than one primer pair, each flanking different SNPs, a minisequencing primer extension reaction is performed in a single well using chain terminator nucleotides. The size of reaction products is determined directly by MALDI-TOF mass spectrometry, yielding the genotype information. It should be possible based upon this teaching. Multiplexing permits determination of, for example, at least 2, 3, 4, and 5 SNPs in a single well of a, for example 384 well plate. For example, at least 6, 7, 8, 9, 10-12-plex genotyping can be performed using the MASSARRAY™ system. The MASSARRAY™ system, for example, can be used to increase the multiplexity level of the genotyping reactions to even higher, for example at least 12-15, 20, 30, 40, and 50-100 and even higher.

Alternatively, fragment analysis for SNP detection can be performed on batches of several samples on a capillary electrophoresis system, for example an ABI PRISM® 3100 GENETIC ANALYZER (Applied Biosystems, Foster City, Calif.). For capillary electrophoretic analysis, the primers can be labeled using dyes, including, but not limited to FAM, HEX, NED, LIZ, ROX, TAMRA, PET and VIC.

Single SNP allelic discrimination can further be carried out using the ABI PRISM® 7900HT Sequence Detection System (Applied Biosystems, Foster City, Calif.), which allows analysis of single nucleotide polymorphisms (SNPs) using the fluorogenic 5' nuclease assay.

Yet another available method useful according to the present invention is an Arrayed Primer Extension (APEX) which is a resequencing method for rapid identification of polymorphisms that combines the efficiency of an microarray-based assay (alternative to gel-based methods, see, e.g., U.S. Pat. No. 6,153,379 and Shumaker et al. Hum. Mutat. 7(4):346-354, 1996) with the Sanger nucleic acid sequencing method (Sanger et al., Proc. Natl. Acad. Sci. 74:5463-5467 (1977)). Generally, microarrays are microchips, for example glass slides, containing thousands of DNA segments in an ordered array, witch allows the simultaneous analysis of thousands of genetic markers.

A yet another genotyping method useful according to the present invention is a solid-phase mini-sequencing technique, which is also based upon a primer extension reaction and can be used for genotyping of SNPs and can also be easily automated (U.S. Pat. No. 6,013,431, Suomalainen et al. Mol. Biotechnol. June; 15(2):123-31, 2000).

In general, a primer extension reaction is a modified cycle sequencing reaction in which at least one dideoxynucleotide (terminator) is present and not all deoxynucleotides are present at any significant concentration. When a terminator is incorporated onto a DNA strand, no further extension can occur on that strand. In a standard cycle sequencing reaction, terminators are present only in small concentrations along with high concentrations of typical nucleotides. In the single base extension reactions for SNP assays, two or more fluorescently or radioactively labeled terminator nucleotides (corresponding to the two or more alleles present at the SNP to be typed) are used.

The steps of the method of the present invention include diluting the nucleic acid sample into single nucleotide dilution, amplifying the diluted sample, and genotyping the amplified sample. These steps are repeated at least 3 times, preferably at least 4, 5, 6, 7, 8, 9, 10-15, 15-20, 20-25, or even 25-50 times. Preferably, the steps are repeated about 12-18 times so that the results can be statistically analyzed. The Poisson distribution analysis is used to analyze the results using the methods known to one skilled in the art. The analysis is described in detail, for example in Stephens et al. Am J Hum Genet 46: 1149-1155, 1990.

Haplotype is defined as a combination of alleles or nucleic acid polymorphisms, such as SNPs of closely linked loci that are found in a single chromosome and which tend to be inherited together. Recombinations occur at different frequency in different parts of the genome and therefore, the length of the haplotypes vary throughout the chromosomal regions and chromosomes. For a specific gene segment, there are often many theoretically possible combinations of SNPs, and therefore there are many theoretically possible haplotypes.

Traditionally, information about gene flow in a pedigree has been used to reconstruct likely haplotypes for families and individuals. However, even if nucleic acid samples from all the family members were available, which is rarely the case, statistics-based haplotype analysis does frequently not reveal the correct phase, i.e. haplotype, of the markers. Additionally, collection of large sample materials from, for example human families, is time consuming and expensive. In one embodiment, the present invention provides a method wherein novel haplotypes are determined using either established or novel nucleic acid polymorphisms. For example, novel SNPs are first identified using nucleic acid samples isolated from several subject organisms of the same species, each polymorphic SNP marker from a subject is then genotyped individually, for example using about 1-10 ng, preferably about 5 ng genomic DNA. The genomic DNA sample is then diluted into about 1 copy of genomic template per dilution. The haplotype is determined by determining the SNP's in a diluted sample, i.e., sample diluted into a substantially single molecule dilution. Alternatively, the sample can be genotyped first or in parallel for each maker using more concentrated nucleic acid solution. This can be used to verify or control the haplotype determination using the diluted sample replicas.

The genomic region to be haplotyped using the method of the present invention is preferably at least about 1, 2, 3, 4, 5, 6, 7, 8, or 9 kb, more preferably at least about 10 kb or more, at least about 15 kb or more, at least about 20 kb or more. In one embodiment, the size of the region containing the polymorphic nucleotides is at least about 25 kb or more, at least about 35 kb or more, at least about 40-45 kb, or 45-50 or even about 50-100 kb or more. Most preferably the genomic region is about 25 kb ore more.

In determining the haplotypes, both the PCR and the genotyping reactions are preferably "multiplexed" which term is meant to include combining at least two, preferably more than at least 3, 4, 5, 6, 7, 8, 9, 10-15, or 20-25 extension primers in the same reaction are used to identify, preferably at least about 3, 4, 5, 6, 7, 8, 9, 10-15, or 20-25 polymorphic nucleic acid regions in the same genotyping reaction. In one embodiment, at least 30 primer pairs or more are used.

In one embodiment, the polymorphism is at least one nucleic acid modification, such as a methylation difference. In one embodiment, the present invention provides a method of determining haplotypes comprised of markers including methylation differences. The method of haplotyping methylation differences according to the present invention comprises the steps of diluting a nucleic acid sample from a subject organism into two parallel substantially single molecule dilutions. The two dilutions are consequently subjected to a methylation detection assay, for example, an AFLP assay (see, e.g., Vos et al. Nucleic Acids Res 23: 4407-4414, 1995; Xu et al., Plant Molecular Biology Reporter 18: 361-368, 2000). The assay described by Vos et al. and Xu et al is modified to perform according the method of present invention.

In short, two single molecule dilutions are digested in two parallel reactions with a mixture comprising a methylation sensitive enzyme and another enzyme, preferably a less frequent cutting restriction enzyme, wherein the less frequent cutting restriction enzyme in both digestion reactions is the same and the methylation sensitive enzymes added to the two parallel reactions differ in their capacity to digest methylated/non-methylated nucleic acids. For example, one dilution is digested with a combination of EcoRI and HpaII and the parallel dilution is treated digested with EcoRI and MspI. The two digested samples are then ligated using an adapter-ligation solution as described in Vos et al. and Xu et al., and amplified in parallel reactions using at least two, preferably more than two primer pairs which are capable of recognizing the restriction enzyme recognition sites in the templates. In the above-described example, EcoRI and HpaII-MspI primers are used. One of the primers is labeled so as to allow detection of the fragments from the digestions using, for example gel electrophoretic methods or mass spectrometric detection.

The methylation detection procedure as described above is repeated at least 3 more times, preferably at least about 6-12 times so as to allow statistical analysis of the correct methylation haplotype in the subject organism.

In light of this disclosure, other nucleic acid modification detection technologies including methylation detection techniques may be readily adapted to be used according to the principle steps of the present invention including single molecule dilution, digestion, multiplex amplification and multiplex genotyping. Methylation detection methods may also be combined to detect both methylation and other polymorphic markers, such as SNPs. In such embodiment, the amplification after restriction enzyme digestion is performed not only with methylation specific primers but also with primers designed to amplify fragments containing known nucleic acid polymorphisms, such as SNPs.

In one embodiment, the invention provides a method of creating haplotypes of several polymorphic nucleotides using overlapping multiplex genotyping assays with single DNA molecules. For example, markers from a large genomic region are chosen and one or more separate multiplex amplification reactions are performed from single nucleotide dilutions and overlapping heterozygous polynucleotide markers are used to obtain the entire haplotype.

Figure 3:
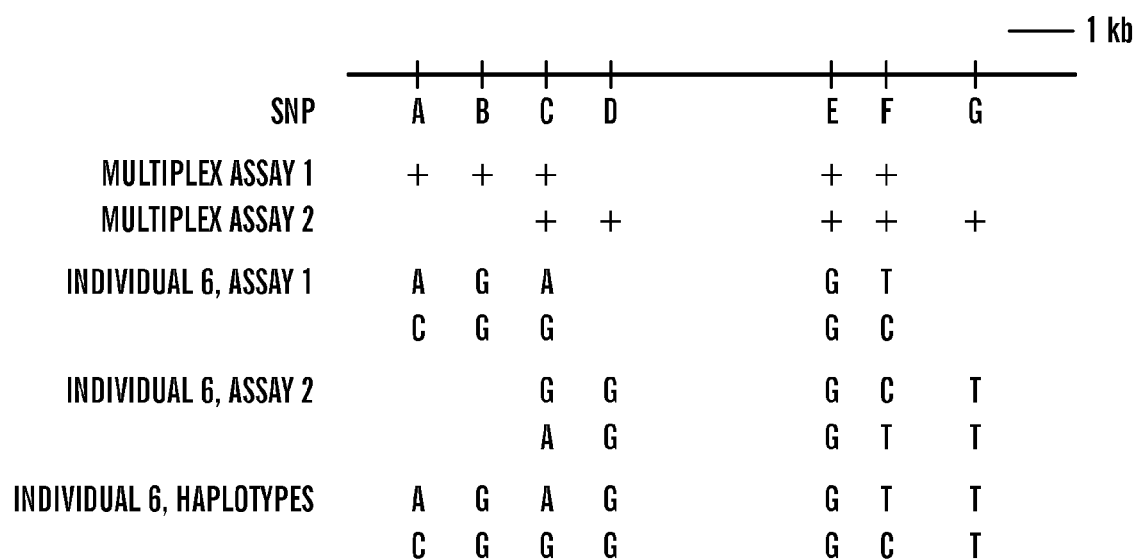
FIG. 3 shows overlapping multiplex genotyping assays with single DNA molecules. Seven SNP markers (A: rs289744, B: rs2228667, C: rs5882, D: rs5880, E: rs5881, F: rs291044, G: 2033254) from an 8 kb genomic region of the CETP locus were chosen (details of these SNPs, their chromosome position and oligonucleotides used for genotyping are provided in Table 2). Two 5-plex genotyping assays were designed for these 7 markers and the overlapping heterozygous SNPs were used to obtain the entire haplotype of 7 SNP markers. Assays on individual 6 were used to demonstrate how this is carried out. Multiplex assay 1 determined the haplotype of 5 SNPs as AGAGT and CGGGC. Multiplex assay 2 determined the other haplotype of 5 SNPs as GGGCT and AGGTT. Then, the genotypes of the overlapping SNPs (SNP C, E, F) were used to combine the two 5-SNP haplotypes into a haplotype of 7 SNPs covering the entire region under investigation.

For example, FIG. 3 shows seven SNP markers (A: rs289744, B: rs2228667, C: rs5882, D: rs5880, E: rs5881, F: rs291044, G: 2033254) from an 8 kb genomic region of the CETP locus that were chosen to determine a haplotype. Details of these SNPs, their chromosome position and oligonucleotides used for genotyping are provided in Table 2. Two 5-plex genotyping assays were designed for the 7 markers and the overlapping heterozygous SNPs were used to obtain the entire haplotype of 7 SNP markers. Assays on individual No. 6 were used to demonstrate how this is carried out. Multiplex assay 1 determined the haplotype of 5 SNPs as AGAGT and CGGGC. Multiplex assay 2 determined the other haplotype of 5 SNPs as GGGCT and AGGTT. Then, the genotypes of the overlapping SNPs (SNP C, E, F) were used to combine the two 5-SNP haplotypes into a haplotype of 7 SNPs covering the entire region under investigation.

EXAMPLE

The effects of genomic DNA concentration on haplotyping efficiency were determined as follows. We used 3 picograms (pg), 5 pg and 9 pg (equivalent of 1, 1.6 and 3 genomic template copies) of genomic DNA for PCR amplification and genotyping of 3 SNPs in the CETP region from 12 individuals. Each 3-plex assay was repeated 12-18 times to evaluate the PCR and haplotyping efficiency. A typical assay result is summarized in Table 1. The copy number of the genomic DNA region of interest for very dilute DNA solutions is estimated by the Poisson distribution[13]. Haplotyping results were categorized into 4 groups (Table 1).

Failed assays can result from either failed PCR amplification from single copy DNAs or simply no template present due to stochastic fluctuation of very dilute DNA solutions.

Partially failed genotyping calls (or incomplete multiplexes) are those that have only 1 or 2 SNPs successfully genotyped. This is most likely due to unsuccessful PCR for 1 or 2 of the SNP DNA regions, since in most cases the 3 SNP markers are present or absent at the same time due to the close proximity of the SNP markers (<628 bp). Poisson distribution may also result in the presence both alleles in the solution and hence the inability to resolve the phase of the SNPs.

Successful haplotyping analysis is achieved when a single copy of the allele or multiple copies of the same allele are present and the genotyping is successful.

Figure 2:
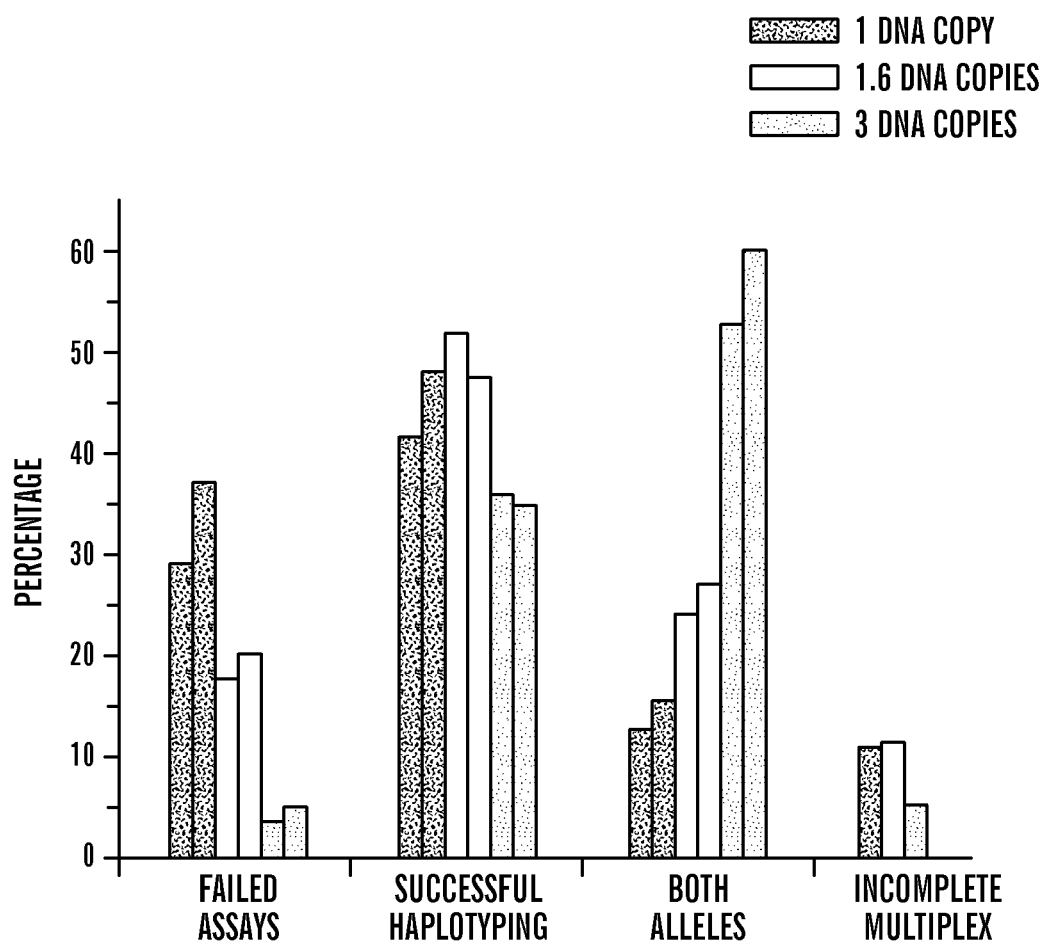
FIG. 2 shows effects of genomic DNA concentration on haplotyping efficiency. About 3 pg, 5 pg and 9 pg (or 1, 1.6 and 3 copies of human genomic templates, respectively) were used for haplotyping of three SNP markers in the CETP region. The DNA copy number in a specific reaction was estimated by the Poisson distribution. The haplotyping result can either be a failed assay, successful haplotyping, both alleles present (no phase determination for the markers), or an incomplete multiplex. Except for incomplete multiplexes, values are percentages from 54 to 144 individual multiplex assays (see specification and example for details on the calculation), followed by predicted values using the Poisson distribution.

Incomplete multiplex genotyping can be used to estimate the efficiency of genotyping from single copy DNA molecules. A partial genotyping call suggests the presence of the SNP DNA but a failure to genotype some of the SNPs. We typically observed 5-10% incomplete multiplex genotyping calls (FIG. 2), suggesting a PCR efficiency of about 90-95% with single DNA molecules. This approach may overestimate the PCR efficiency, since we did not take the completely failed assays into account. We also carried out detailed comparison between observed and theoretical values of failed assays, successful haplotyping and the presence of both alleles (FIG. 2 and see methods section for details of calculation). Theoretical values are based on the Poisson distribution of very dilute DNA solutions and the assumption of 100% PCR amplification efficiency. The close agreement between theoretical estimate and experimental observation substantiates the earlier estimate of extremely high PCR efficiency with single DNA molecules.

High PCR efficiency is mainly due to the high efficiency of amplification of very short amplicons (typically 100 bp) and the high sensitivity of MALDI-TOF mass spectrometric detection of DNA oligonucleotides. High PCR efficiency is preferred for high-throughput haplotyping analysis. For example, with our current PCR efficiency, we can achieve 40-45% haplotyping efficiency with one single reaction using 3-4.5 pg genomic DNA. A replicate of 4 independent multiplex genotyping assays will enable about 90% of direct haplotyping efficiency.

We next demonstrated an approach for determining haplotypes where there are too many markers to be determined in one multiplex genotyping assay. Overlapping informative SNPs were used to combine haplotypes from several multiplex assays. We chose six SNP markers in an 8 kb CETP genomic region, and 2 overlapping 4-plex genotyping assays were used for haplotyping analysis (FIG. 3). We were able to determine the haplotypes of all 12 individuals for this genomic region, with absolutely no optimization of the assay system.

The approach presented here provides a powerful and unique technology platform for direct molecular haplotyping analysis of long-range genomic regions. This approach is completely independent of pedigree genotype information.

We have further incorporated this technique with the commercially available MASSARRAY™ system for high-throughput applications. This technology is extremely useful in large-scale haplotyping and haplotype-based diagnostics.

Materials and Methods

Genomic DNAs and oligo nucleotides. Human genomic DNA samples used for haplotyping of the CETP locus were provided by SEQUENOM Inc. (San Diego, Calif.). These DNAs were isolated using the Puregene DNA isolation kit (Gentra Systems) from blood samples purchased from the Blood Bank (San Bernadino County, CA). The personal background of the blood donors is not accessible for these samples. Human genomic DNAs samples for haplotyping of a 25 kb segment on chromosome 5q31 were CETP family DNAs purchased from Coriell Cell Repositories (see Table 3). Information on SNPs and oligonucleotides for genotyping is provided in Table 2.

Genotyping and haplotyping analysis. Genotyping analyses were carried out using the MassArray™ system (SEQUENOM Inc.). Each SNP from every individual was first genotyped individually using 5 ng genomic DNA. For haplotyping analysis, multiplex genotyping assays were carried out using 3 pg (or approximately 1 copy of genomic template, unless otherwise specified) genomic DNA.

Analysis of effects of genomic DNA concentration on haplotyping. To calculate the percentage of failed assays, we simply counted all failed assays (no calls for either SNP), divided by the total number of assays. We typically do 12 to 18 replicates for each 6 or 12 individuals. The percentage of incomplete assays is calculated in the same way. To calculate percentage of successful haplotyping and both alleles, we excluded the data from those individuals with homozygous haplotypes. Theoretical predictions are based on the Poisson distribution of very diluted DNA solutions, according to a published method[13].

TABLE 1

Sample Haplotype analysis with triplex genotyping assay[a]

| Repeat | Genotype Calls |
|---|---|
| 1 | GGC[b] |
| 2 | GGC |

TABLE 1-continued

Sample Haplotype analysis with triplex genotyping assay[a]

| Repeat | Genotype Calls |
|---|---|
| 3 | —[c] |
| 4 | -GC[d] |
| 5 | — |
| 6 | GGC |
| 7 | — |
| 8 | ACA |
| 9 | -GC |
| 10 | A/G C/G A/C[e] |
| 11 | ACA |
| 12 | ACA |

[a]Genotypes of 3 SNP markers were determined with triplex assays from 3 pg genomic DNA.
[b]The 3 SNPs are G, G, C genotype respectively.
[c]Failed to genotype any of the 3 SNPs.
[d]Failed to genotype the first SNP, the rest two SNPs are G and C respectively.
[e]Failed to separate the two alleles, thus the genotypes are A/G, C/A and A/C for the 3 SNPs.

TABLE 2

Single nucleotide polymorphism (SNP) markers, their chromosomal locations, primer pairs to amplify the markers and terminator mixes used in the reaction.

| SNP ID | Chrom. Position | PCR primer 1 | PCR primer 2 | Extension Primer | Term. Mix |
|---|---|---|---|---|---|
| rs289741 | 47282625 | TCTACCAGCTTGGCTCCCTC (SEQ ID NO.: 1) | AAGTCCATCAGCAGCAGCAG (SEQ ID NO.: 2) | GGGAGTCAGCCCAGCTC (SEQ ID NO.: 3) | ACT |
| rs289742 | 47282337 | ACTGGTGAGACAATCCCTTC (SEQ ID NO.: 4) | CCACTGGCATTAAAGTGCTG (SEQ ID NO.: 5) | AGCCACAGAAGAAGGACTCC (SEQ ID NO.: 6) | ACT |
| rs289744 | 47281997 | TACCAGAAACCAGACCTCTG (SEQ ID NO.: 7) | AGTGCTGGACAGAAAGTGAG (SEQ ID NO.: 8) | TGAGGATGGTGGGAGGG (SEQ ID NO.: 9) | ACT |
| rs289744[a] | 47281997 | TCTACCAGAAACCAGACCTC (SEQ ID NO.: 10) | AGTGCTGGACAGAAAGTGAG (SEQ ID NO.: 11) | ACCTCTGAGGGCCCCTTAC (SEQ ID NO.: 12) | CG |
| rs2228667[a] | 47282820 | CTCGAGTGATAATCTCAGGG (SEQ ID NO.: 13) | AGGTAGTGTTTACAGCCCTC (SEQ ID NO.: 14) | TGATGATGTCGAAGAGGCTCATG (SEQ ID NO.: 15) | CG |
| rs5882[a] | 47284007 | TTACGAGACATGACCTCAGG (SEQ ID NO.: 16) | GCATTTGATTGGCAGAGCAG (SEQ ID NO.: 17) | CTGCAGGAAGCTCTGGATG (SEQ ID NO.: 18) | CG |
| rs5882[b] | 47284007 | GCATTTGATTGGCAGAGCAG (SEQ ID NO.: 19) | TTACGAGACATGACCTCAGG (SEQ ID NO.: 20) | AGAGCAGCTCCGAGTCC (SEQ ID NO.: 21) | ACT |

TABLE 2-continued

Single nucleotide polymorphism (SNP) markers, their chromosomal locations, primer pairs to amplify the markers and terminator mixes used in the reaction.

| SNP ID | Chrom. Position | PCR primer 1 | PCR primer 2 | Extension Primer | Term. Mix |
|---|---|---|---|---|---|
| rs5880[b] | 47285008 | GCAGCACATACTGGAAATCC (SEQ ID NO.: 22) | TTTCTCTCCCCAGGATATCG (SEQ ID NO.: 23) | GCTTTTTCTTAGAATAGGAGG (SEQ ID NO.: 24) | ACT |
| rs5881[a] | 47288087 | AGATCTTGGGCATCTTGAGG (SEQ ID NO.: 25) | ACCCCTGTCTTCCACAGGTT (SEQ ID NO.: 26) | TGGGCCTGGCTGGGGAAGC (SEQ ID NO.: 27) | CG |
| rs5881[b] | 47288087 | ACCCCTGTCTTCCACAGGTT (SEQ ID NO.: 28) | AGATCTTGGGCATCTTGAGG (SEQ ID NO.: 29) | TGTCTTCCACAGGTTGTCGGC (SEQ ID NO.: 30) | ACT |
| rs291044[a] | 47288647 | GTAAAACTGCAGCTGAGGAG (SEQ ID NO.: 31) | TGACTAGGTCAGGTCCCCTC (SEQ ID NO.: 32) | GGAGTATTTAAAGGAGAGACACACTAG (SEQ ID NO.: 33) | CG |
| rs291044[b] | 47288647 | TGACTAGGTCAGGTCCCCTC (SEQ ID NO.: 34) | GTAAAACTGCAGCTGAGGAG (SEQ ID NO.: 35) | CCCTCGTGCCACAGCCT (SEQ ID NO.: 36) | ACT |
| rs2033254[b] | 47290114 | GGACATCAAAGGAACAGGAC (SEQ ID NO.: 37) | ACTCACAATATTGGGCAGGC (SEQ ID NO.: 38) | CAAGGGGCTAAGGGAGAAG (SEQ ID NO.: 39) | ACT |
| IGR2198A_1[c] | 506266d | GGGTTGCATGAGCATTAAGT (SEQ ID NO.: 40) | CACATCAAGGATAAGACTGC (SEQ ID NO.: 41) | ATCTCTTCAGTAGACGAAC (SEQ ID NO.: 42) | AC |
| IGR2175A_2 | 495082 | TGGCCTTGATTCAAACCCTG (SEQ ID NO.: 43) | AGATGAAGGAAATCCCAAGG (SEQ ID NO.: 44) | TGCCACTAACATACATAGTAAC (SEQ ID NO.: 45) | AC |
| IGR2150A_1 | 482171 | CCTTGGCTTGATAGTCAAAC (SEQ ID NO.: 46) | ATTTGGAGGAGTGCAGAGAG (SEQ ID NO.: 47) | AGTCAAACTCTCACCAC (SEQ ID NO.: 48) | AC |

[a]Multiplex Group a
[b]Multiplex Group b
[c]SNP ID from ref
[d]position of SNP from ref
Term. Mix = terminator nucleotide mix. Chrom. Position = chromosomal position

TABLE 3

DNA samples used in the Example.

| Repository Number | Sample Type | Sample Description | Relation |
|---|---|---|---|
| GM12547 | Lymphoblast | CEPH/FRENCH PEDIGREE 66 | father |
| GM12548 | Lymphoblast | CEPH/FRENCH PEDIGREE 66 | mother |
| GM12549 | Lymphoblast | CEPH/FRENCH PEDIGREE 66 | son |
| GM12550 | Lymphoblast | CEPH/FRENCH PEDIGREE 66 | daughter |
| GM12551 | Lymphoblast | CEPH/FRENCH PEDIGREE 66 | daughter |
| GM12552 | Lymphoblast | CEPH/FRENCH PEDIGREE 66 | son |
| GM12553 | Lymphoblast | CEPH/FRENCH PEDIGREE 66 | daughter |
| GM12554 | Lymphoblast | CEPH/FRENCH PEDIGREE 66 | daughter |
| GM12555 | Lymphoblast | CEPH/FRENCH PEDIGREE 66 | son |
| GM12556 | Lymphoblast | CEPH/FRENCH PEDIGREE 66 | paternal grandfather |
| GM12557 | Lymphoblast | CEPH/FRENCH PEDIGREE 66 | paternal grandmother |
| GM12558 | Lymphoblast | CEPH/FRENCH PEDIGREE 66 | maternal grandfather |
| GM12559 | Lymphoblast | CEPH/FRENCH PEDIGREE 66 | maternal grandmother |
| GM07038 | Lymphoblast | CEPH/UTAH PEDIGREE 1333 | father |
| GM06987 | Lymphoblast | CEPH/UTAH PEDIGREE 1333 | mother |
| GM07004 | Lymphoblast | CEPH/UTAH PEDIGREE 1333 | son |
| GM07052 | Lymphoblast | CEPH/UTAH PEDIGREE 1333 | son |
| GM06982 | Lymphoblast | CEPH/UTAH PEDIGREE 1333 | son |
| GM07011 | Lymphoblast | CEPH/UTAH PEDIGREE 1333 | daughter |
| GM07009 | Lymphoblast | CEPH/UTAH PEDIGREE 1333 | son |
| GM07678 | Lymphoblast | CEPH/UTAH PEDIGREE 1333 | son |
| GM07026 | Lymphoblast | CEPH/UTAH PEDIGREE 1333 | son |

TABLE 3-continued

DNA samples used in the Example.

| Repository Number | Sample Type | Sample Description | Relation |
|---|---|---|---|
| GM07679 | Lymphoblast | CEPH/UTAH PEDIGREE 1333 | son |
| GM07049 | Lymphoblast | CEPH/UTAH PEDIGREE 1333 | paternal grandfather |
| GM07002 | Lymphoblast | CEPH/UTAH PEDIGREE 1333 | paternal grandmother |
| GM07017 | Lymphoblast | CEPH/UTAH PEDIGREE 1333 | maternal grandfather |
| GM07341 | Lymphoblast | CEPH/UTAH PEDIGREE 1333 | maternal grandmother |
| GM11820 | Lymphoblast | CEPH/UTAH PEDIGREE 1333 | daughter |
| GM07029 | Lymphoblast | CEPH/UTAH PEDIGREE 1340 | father |
| GM07019 | Lymphoblast | CEPH/UTAH PEDIGREE 1340 | mother |
| GM07062 | Lymphoblast | CEPH/UTAH PEDIGREE 1340 | daughter |
| GM07053 | Lymphoblast | CEPH/UTAH PEDIGREE 1340 | daughter |
| GM07008 | Lymphoblast | CEPH/UTAH PEDIGREE 1340 | son |
| GM07040 | Lymphoblast | CEPH/UTAH PEDIGREE 1340 | son |
| GM07342 | Lymphoblast | CEPH/UTAH PEDIGREE 1340 | son |
| GM07027 | Lymphoblast | CEPH/UTAH PEDIGREE 1340 | son |
| GM06994 | Lymphoblast | CEPH/UTAH PEDIGREE 1340 | paternal grandfather |
| GM07000 | Lymphoblast | CEPH/UTAH PEDIGREE 1340 | paternal grandmother |
| GM07022 | Lymphoblast | CEPH/UTAH PEDIGREE 1340 | maternal grandfather |
| GM07056 | Lymphoblast | CEPH/UTAH PEDIGREE 1340 | maternal grandmother |
| GM11821 | Lymphoblast | CEPH/UTAH PEDIGREE 1340 | son |
| GM07349 | Lymphoblast | CEPH/UTAH PEDIGREE 1345 | father |
| GM07348 | Lymphoblast | CEPH/UTAH PEDIGREE 1345 | mother |
| GM07350 | Lymphoblast | CEPH/UTAH PEDIGREE 1345 | daughter |
| GM07351 | Lymphoblast | CEPH/UTAH PEDIGREE 1345 | son |
| GM07352 | Lymphoblast | CEPH/UTAH PEDIGREE 1345 | son |
| GM07353 | Lymphoblast | CEPH/UTAH PEDIGREE 1345 | son |
| GM07354 | Lymphoblast | CEPH/UTAH PEDIGREE 1345 | daughter |
| GM07355 | Lymphoblast | CEPH/UTAH PEDIGREE 1345 | son |
| GM07356 | Lymphoblast | CEPH/UTAH PEDIGREE 1345 | son |
| GM07347 | Lymphoblast | CEPH/UTAH PEDIGREE 1345 | paternal grandfather |
| GM07346 | Lymphoblast | CEPH/UTAH PEDIGREE 1345 | paternal grandmother |
| GM07357 | Lymphoblast | CEPH/UTAH PEDIGREE 1345 | maternal grandfather |
| GM07345 | Lymphoblast | CEPH/UTAH PEDIGREE 1345 | maternal grandmother |

REFERENCES

The references cited herein and throughout the specification are incorporated herein by reference in their entirety.
1. Grupe, A. et al. In silico mapping of complex disease-related traits in mice. *Science* 292, 1915-8. (2001).
2. Hirschhorn, J. N., Lohmueller, K., Byrne, E. & Hirschhorn, K. A comprehensive review of genetic association studies. *Genet Med* 4, 45-61. (2002).
3. Zhang, S., Pakstis, A. J., Kidd, K. K. & Zhao, H. Comparisons of two methods for haplotype reconstruction and haplotype frequency estimation from population data. *Am J Hum Genet* 69, 906-14. (2001).
4. Templeton, A. R., Sing, C. F., Kessling, A. & Humphries, S. A cladistic analysis of phenotype associations with haplotypes inferred from restriction endonuclease mapping. II. The analysis of natural populations. *Genetics* 120, 1145-54. (1988).
5. Kruglyak, L. Prospects for whole-genome linkage disequilibrium mapping of common disease genes. *Nat Genet* 22, 139-44. (1999).
6. Judson, R., Stephens, J. C. & Windemuth, A. The predictive power of haplotypes in clinical response. *Pharmacogenomics* 1, 15-26. (2000).
7. Martin, E. R. et al. Analysis of association at single nucleotide polymorphisms in the APOE region. *Genomics* 63, 7-12. (2000).
8. Clark, A. G. Inference of haplotypes from PCR-amplified samples of diploid populations. *Mol Biol Evol* 7, 111-22. (1990).
9. Stephens, M., Smith, N. J. & Donnelly, P. A new statistical method for haplotype reconstruction from population data. *Am J Hum Genet* 68, 978-89. (2001).
10. Ruano, G. & Kidd, K. K. Direct haplotyping of chromosomal segments from multiple heterozygotes via allele-specific PCR amplification. *Nucleic Acids Res* 17, 8392. (1989).
11. Ruano, G., Kidd, K. K. & Stephens, J. C. Haplotype of multiple polymorphisms resolved by enzymatic amplification of single DNA molecules. *Proc Natl Acad Sci USA* 87, 6296-300. (1990).
12. Douglas, J. A., Boehnke, M., Gillanders, E., Trent, J. M. & Gruber, S. B. Experimentally-derived haplotypes substantially increase the efficiency of linkage disequilibrium studies. *Nat Genet* 28, 361-4. (2001).
13. Stephens, J. C., Rogers, J. & Ruano, G. Theoretical underpinning of the single-molecule-dilution (SMD) method of direct haplotype resolution. *Am J Hum Genet* 46, 1149-55. (1990).
14. Daly, M. J., Rioux, J. D., Schaffner, S. F., Hudson, T. J. & Lander, E. S. High-resolution haplotype structure in the human genome. *Nat Genet* 29, 229-32. (2001).
15. Gabriel, S. B. et al. The structure of haplotype blocks in the human genome. *Science* 296, 2225-9. (2002).

We claim:

1. A method for determining a haplotype comprising at least three polymorphic markers in a subject comprising the steps of:
   (a) diluting a nucleic acid sample from the subject to a single nucleic acid molecule dilution;
   (b) amplifying in one multiplex reaction the single nucleic acid molecule dilution with at least a first, a second and a third primer pair, wherein each primer pair flanks a nucleic acid region consisting of about 50 bp, each primer pair thereby producing an amplicon consisting of about 50 bp, and wherein the at least first, second and third primer pair each are designed to amplify a different nucleic acid region designated as a first, a second and a third nucleic acid region;
   (c) genotyping the polymorphic site in the at least first, second, and third nucleic acid region using primer extension and mass spectrometric detection thereby resulting in at least a first, a second and a third genotype; and
   (d) determining the haplotype comprising polymorphic markers from the at least the first, the second and the third genotype to obtain a haplotype for the subject.

2. The method of claim 1, further comprising repeating steps (a), (b), and (c) at least three times from the nucleic acid sample to obtain at least four genotype replicas from the subject and thereafter subjecting the at least four genotype replicas to a statistical analysis to determine the haplotype.

3. The method of claim 2, further comprising comparing the haplotype with a haplotype from a control or a database of haplotypes from controls to determine association of the haplotype with a biological trait.

4. The method of claim 1, wherein the polymorphic markers are single nucleotide polymorphisms.

5. The method of claim 1, wherein the polymorphic markers are deletions, insertions, substitutions or inversions.

6. The method of claim 1, wherein the polymorphic markers are a combination of one or more markers selected from the group consisting of single nucleotide polymorphisms, deletion, insertions, substitutions or inversions.

7. The method of claim 1, wherein the first, second and third polymorphic markers are about one or more kilo base pairs apart.

8. The method of claim 2, wherein 12-18 genotype replicas are produced.

9. A method of diagnosing a disease condition or disease susceptibility by determining a disease related haplotype comprising at least three polymorphic markers comprising the steps of:
  (a) diluting a nucleic acid sample from the subject into a single nucleic acid molecule dilution;
  (b) amplifying in one multiplex reaction the single nucleic acid molecule dilution with at least a first, a second and a third primer pair, wherein each primer pair flanks a nucleic acid region consisting of about 50 bp, each primer pair thereby producing an amplicon consisting of about 50 bp, and wherein the at least first, second and third primer pair each are each designed to amplify a different region designated as a first, a second and a third nucleic acid region wherein each nucleic acid region comprises at least one polymorphic marker;
  (c) genotyping the polymorphic site in the at least the first, second and third nucleic acid region using primer extension and mass spectrometric detection thereby resulting in at least a first, a second and a third genotype;
  (d) determining the haplotype comprising polymorphic markers from the first, the second and the third genotypes to obtain a haplotype of the subject; and
  (e) comparing the haplotype of the subject to one or more known disease-associated haplotypes, wherein a match in the haplotype of the subject with any one of the known disease-associated haplotypes indicates that the subject has the disease or that the subject is susceptible for the disease.

10. The method of claim 9, further comprising repeating steps (a), (b), and (c) at least three times from the nucleic acid sample to obtain at least four genotype replicas from the subject and thereafter subjecting the at least four genotype replicas to a statistical analysis to determine the haplotype.

11. The method of claim 10, wherein 12-18 replicas are produced.

12. The method of claim 9, wherein the first the second and the third polymorphic markers are one or more kilobase pairs apart.

13. A method of determining a haplotype in a subject, the haplotype comprising at least three polymorphic markers comprising the steps of:
  (a) treating a nucleic acid sample from the subject with a composition that differentially affects an epigenetically modified nucleotide in the nucleic acid sample to effectively create at least a first, a second and a third polymorphic marker in the nucleic acid sample, wherein each marker is a result of an epigenetically modified nucleotide;
  (b) diluting the nucleic acid sample of step (a) into a single nucleic acid molecule dilution;
  (c) amplifying in one multiplex reaction the single nucleic acid copy dilution using at least a first, a second and a third primer pair, wherein each primer pair flanks a nucleic acid region of about 50 bp long each primer pair thereby producing an amplicon consisting of about 50 bp, and wherein the at least first, second and third primer pair each are designed to amplify a different nucleic acid region designated as a first, a second and a third nucleic acid region, wherein the first, the second and the third nucleic acid region each comprise at least one polymorphic marker that is a result of an epigenetically modified nucleotide designated as a first, a second and a third polymorphic marker;
  (d) genotyping the polymorphic marker in the first, second and third nucleic acid regions using primer extension and mass spectrometric detection thereby resulting in at least a first, a second and a third genotype; and
  (e) determining the haplotype comprising polymorphic markers from the first, second and third genotypes to obtain a haplotype for the subjectof the subject from the at least first, the second and the third genotype.

14. The method of claim 13, further comprising repeating the steps (b), (c), and (d) at least three times to obtain at least four genotype replicas from the subject and thereafter determining a haplotype of the subject based on the genotype replicas by subjecting the at least four genotype replicas to a statistical analysis.

15. The method of claim 14, wherein 12-18 replicas are produced.

16. The method of claim 13, wherein the epigenetically modified nucleotide is a methylated nucleotide.

17. The method of claim 16, wherein the nucleic acid sample is treated with bisulfite.

18. The method of claim 13, wherein the first the second and the third polymorphic markers are one or more kilobase pairs apart.

19. A method of determining a haplotype in a subject, the haplotype comprising at least three polymorphic markers, wherein at least one polymorphic marker is a methylated nucleotide, comprising the steps of:
  (a) digesting a nucleic acid sample from the subject with a methylation-sensitive restriction enzyme so that either unmethylated DNA or methylated DNA is left intact, depending on which enzyme is used;
  (b) diluting the digested nucleic acid sample of step (a) into a single nucleic acid molecule dilution;
  (c) amplifying in one multiplex reaction the single nucleic acid molecule dilution with at least a first, a second and a third primer pair, wherein each primer pair flanks a nucleic acid region of about 50 bp long, each primer pair thereby producing an amplicon consisting of about 50 bp, and wherein the at least first, second and third primer pair each amplify a different nucleic acid region designated as a first, a second and a third nucleic acid region, wherein the first, the second and the third nucleic acid region each comprise at least one polymorphic marker, wherein at least one polymorphic marker is a result of a methylated nucleotide;
  (e) genotyping the polymorphic marker in the first, second, and third nucleic acid region using primer extension and mass spectrometric detection thereby resulting in at least a first and a second genotype; and
  (f) determining the haplotype comprising polymorphic markers from the first, second and third genotypes to obtain a haplotype for the subject, wherein at least one polymorphic marker next to a methylation site, together with the methylation site, constitutes a haplotype.

20. The method of claim 19, further comprising repeating the steps (b), (c), (d), (e), and (f) at least three times to obtain at least four genotype replicas from the subject and thereafter determining a haplotype of the subject based on the genotype replicas by subjecting the at least four genotype replicas to a statistical analysis.

21. The method of claim 19, wherein the first the second and the third polymorphic markers are one or more kilobase pairs apart.

22. The method of claim 1, wherein at least 5 primer pairs amplifying at least five different nucleic acid regions are used.

23. The method of claim 1, wherein at least 10 primer pairs amplifying at least 10 different nucleic acid regions are used.

24. The method of claim 1, wherein the at least one polymorphic site in the first nucleic acid region is three or more kilo base pairs apart from the at least one polymorphic site in the second nucleic acid region.

25. The method of claim 1, wherein the at least one polymorphic site in the first nucleic acid region is four or more kilo base pairs apart from the at least one polymorphic site in the second nucleic acid region.

26. The method of claim 1, wherein the at least one polymorphic site in the first nucleic acid region is 15-20 kilo base pairs apart from the at least one polymorphic site in the second nucleic acid region.

* * * * *